United States Patent
Bonutti

Patent Number: 5,295,994
Date of Patent: Mar. 22, 1994

[54] ACTIVE CANNULAS

[76] Inventor: Peter M. Bonutti, 1303 W. Evergreen Plz., Effingham, Ill. 62401

[21] Appl. No.: 792,730

[22] Filed: Nov. 15, 1991

[51] Int. Cl.⁵ .............................................. A61B 17/00
[52] U.S. Cl. ...................... 606/192; 604/96; 604/102; 604/103
[58] Field of Search ............... 604/104, 105, 96–99, 604/102, 103, 27, 264, 280, 174, 175, 164; 128/4; 606/192, 193, 194, 195, 196, 198, 191

[56] References Cited

U.S. PATENT DOCUMENTS

| | | | |
|---|---|---|---|
| 3,039,468 | 1/1959 | Price | 604/49 |
| 3,253,594 | 5/1966 | Matthews et al. | 198/341 |
| 3,459,175 | 8/1969 | Miller | 128/654 |
| 3,788,318 | 1/1974 | Kim et al. | 604/164 |
| 3,789,852 | 2/1974 | Kim et al. | 604/104 |
| 3,850,720 | 11/1974 | Collins | 604/103 |
| 4,077,412 | 3/1978 | Moossun | 604/96 |
| 4,083,369 | 4/1978 | Sinnreich | 604/174 |
| 4,265,848 | 5/1981 | Rüsch | 604/103 |
| 4,434,797 | 3/1984 | Silander | 606/191 |
| 4,461,281 | 7/1984 | Carson | 128/3 |
| 4,535,757 | 8/1985 | Webster, Jr. | 604/104 X |
| 4,540,404 | 9/1985 | Wolvek | 604/96 |
| 4,555,242 | 11/1985 | Saudagar | 604/96 |
| 4,716,901 | 1/1988 | Jackson et al. | 606/185 |
| 4,796,629 | 1/1989 | Grayzel | 604/93 X |
| 4,875,468 | 10/1989 | Krauter et al. | 128/3 |
| 4,899,729 | 2/1990 | Gill et al. | 128/3 |
| 4,927,412 | 5/1990 | Menasche | 604/96 |
| 4,932,956 | 6/1990 | Reddy et al. | 606/192 |
| 4,984,564 | 1/1991 | Yuen | 128/20 |
| 4,994,047 | 2/1991 | Walker et al. | 604/264 |
| 5,002,557 | 3/1991 | Hasson | 606/191 |
| 5,041,125 | 8/1991 | Montano, Jr. | 604/192 |
| 5,042,976 | 8/1991 | Ishitsu et al. | 604/96 |

FOREIGN PATENT DOCUMENTS 0287998 10/1988 European Pat. Off. ............. 604/96

Primary Examiner—Edgar S. Burr
Assistant Examiner—Christopher A. Bennett
Attorney, Agent, or Firm—Tarolli, Sundheim & Covell

[57] ABSTRACT

An active cannula or sleeve which does more than merely maintain a channel or passage is usable to enlarge a channel or passage, to position a scope or instrument, to move or locate tissue, etc. The cannula can vary in size or shape as needed, intraoperatively. Because a cannula of the present invention is expandable, the surgeon can make a small relatively small incision, stretch the tissue with the expandable cannula, contract the cannula and remove it, allowing the skin to come back to its unstretched condition. Thus, a smaller incision can be made to fit the same size instrument. This results in less trauma and scarring and an easier operation. The cannulas are or can assume such a non-circular shape, to fit into a natural skin opening and cause less trauma. The devices can be used to seal off a space; to expand an existing space or a potential space for working or visualization; to move tissue (for example, to stretch an incision) or to protect it.

3 Claims, 14 Drawing Sheets

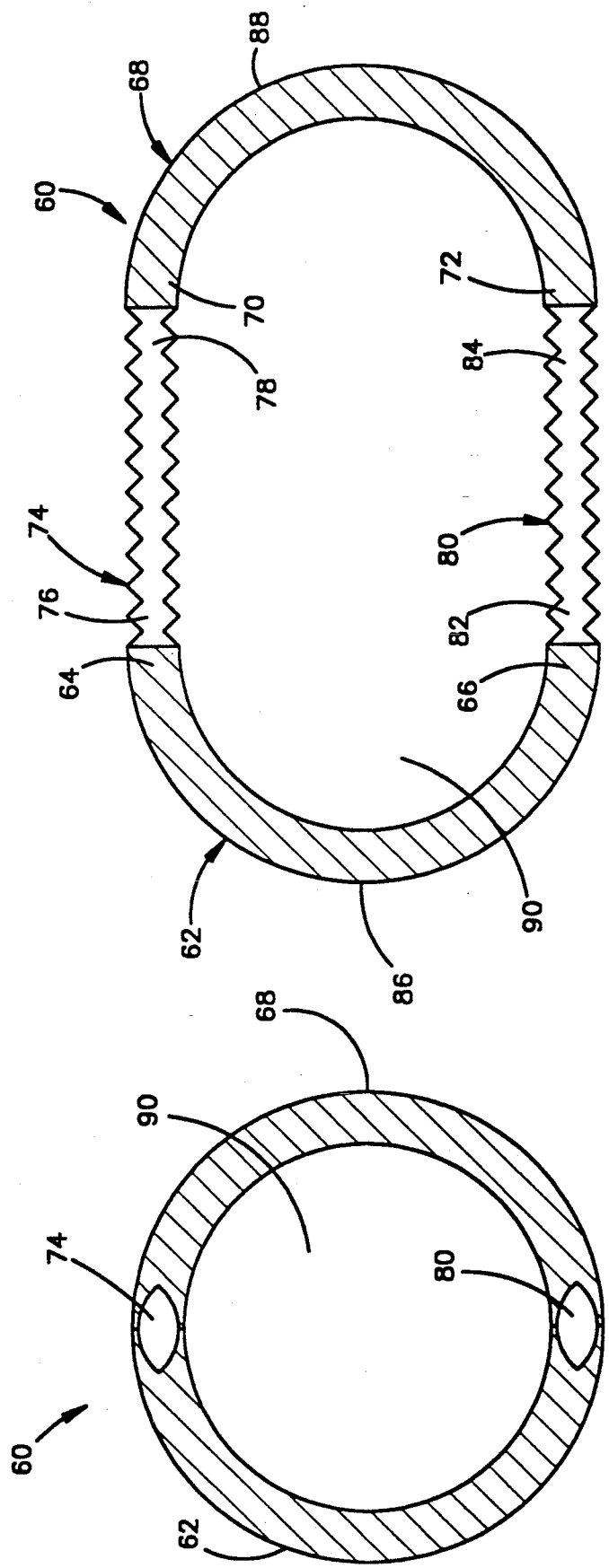

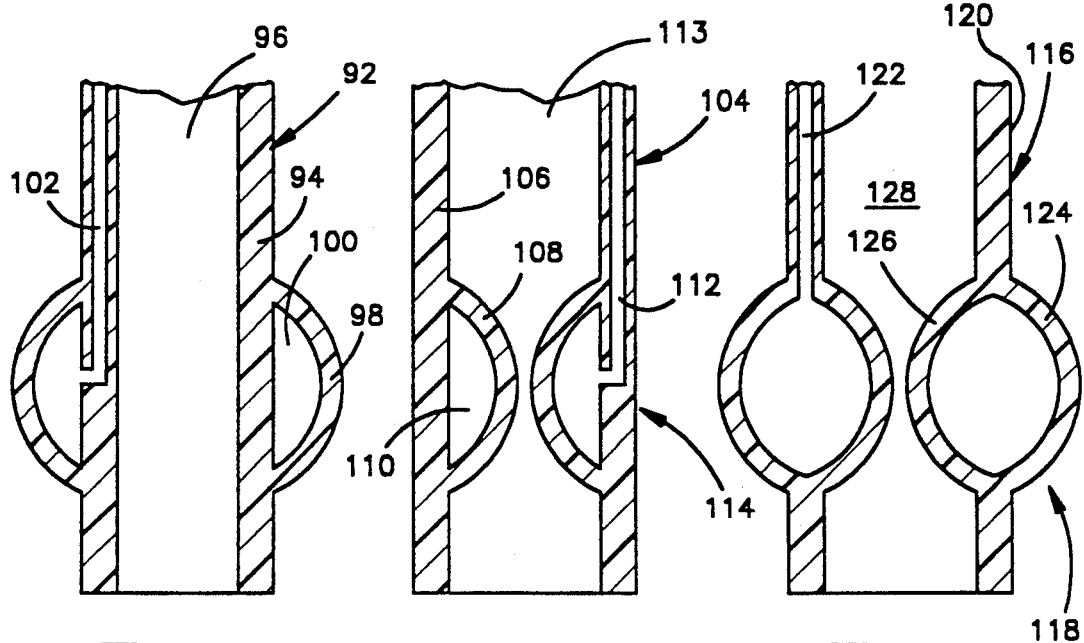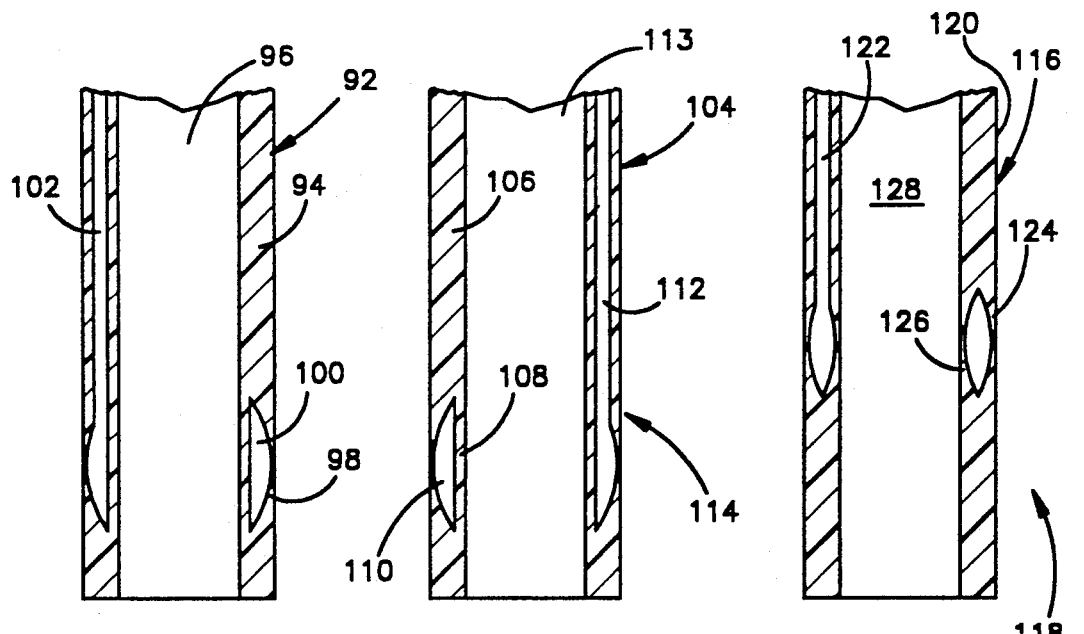

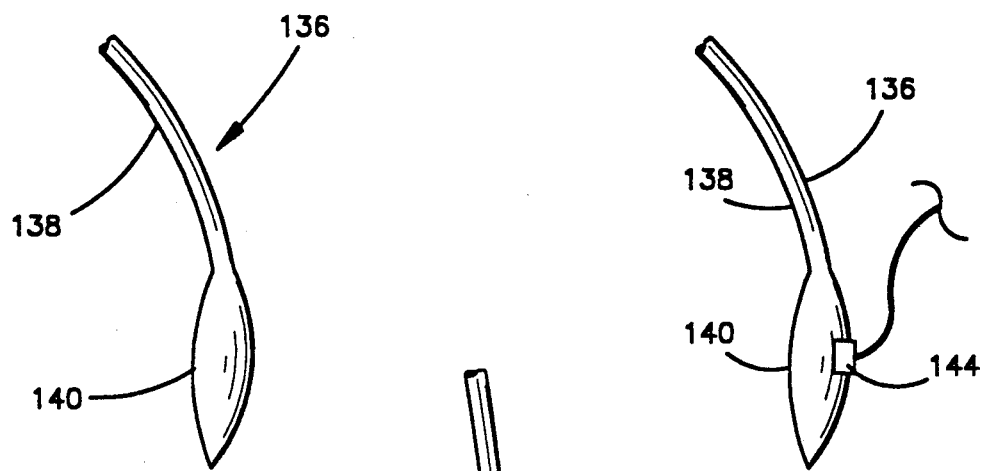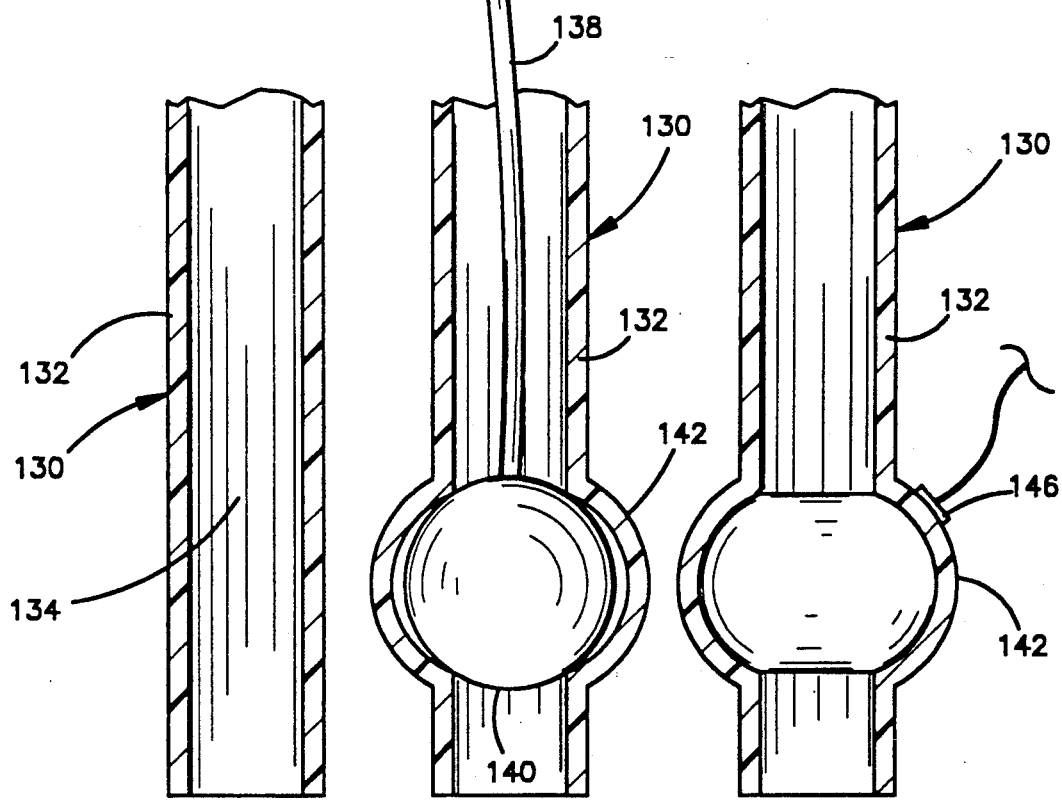
Fig.10A  Fig.10B  Fig.10C

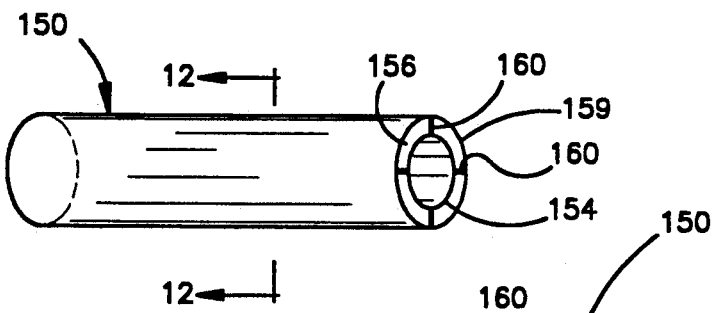
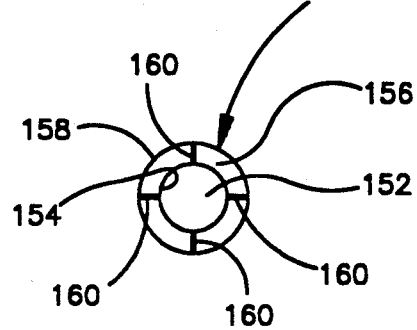
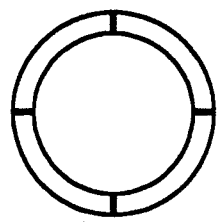
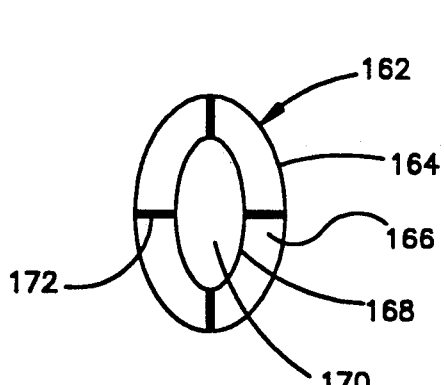
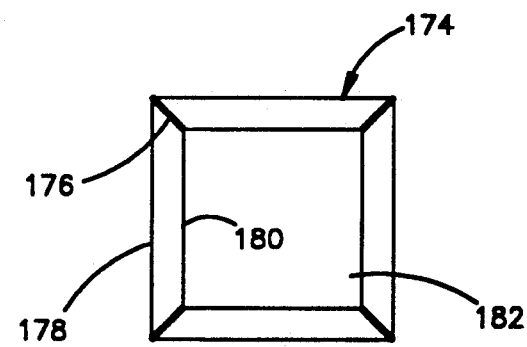
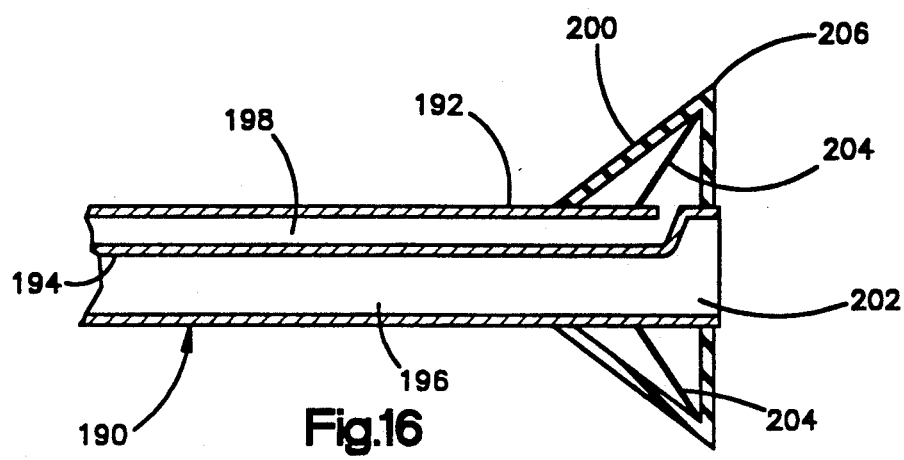

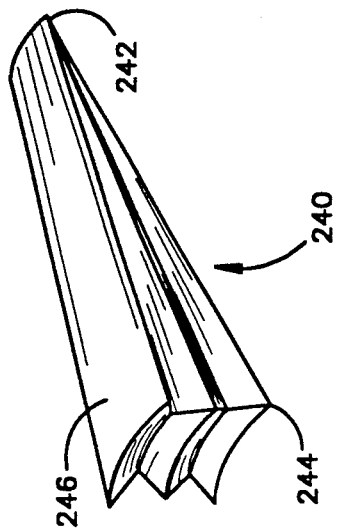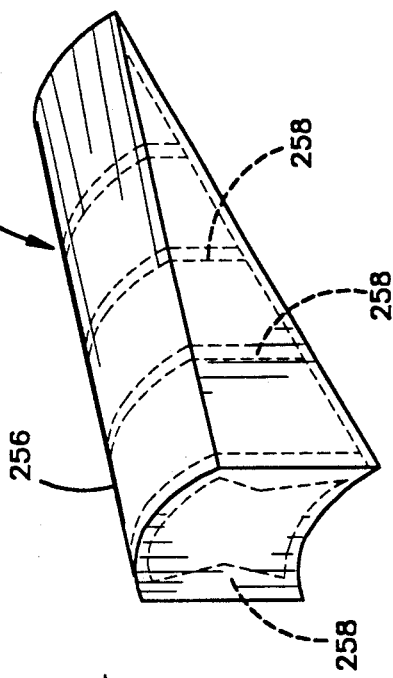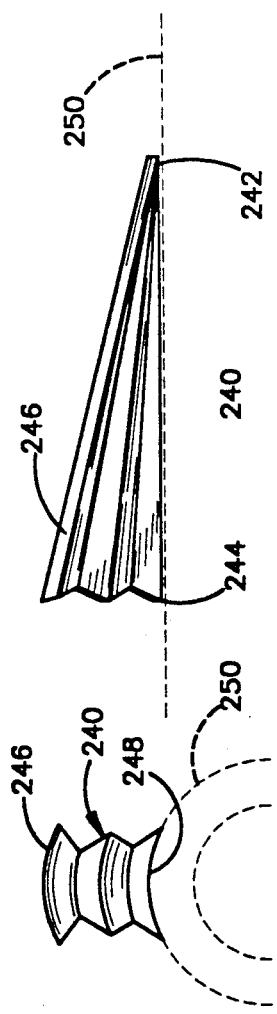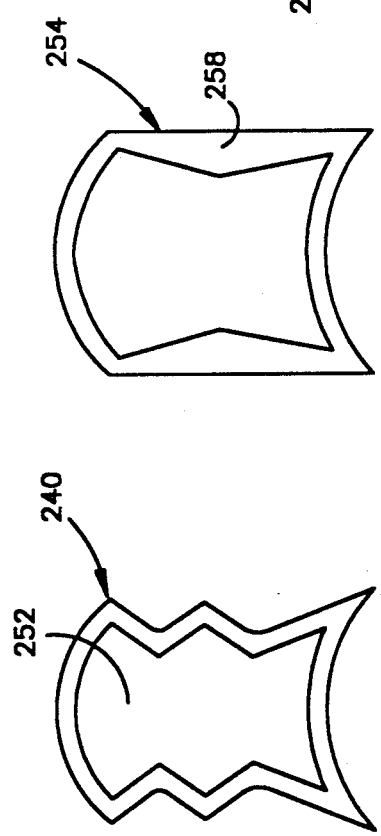

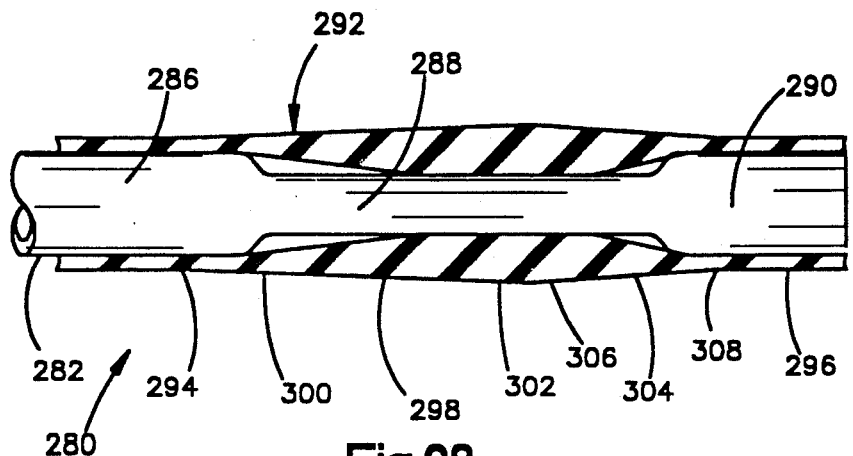
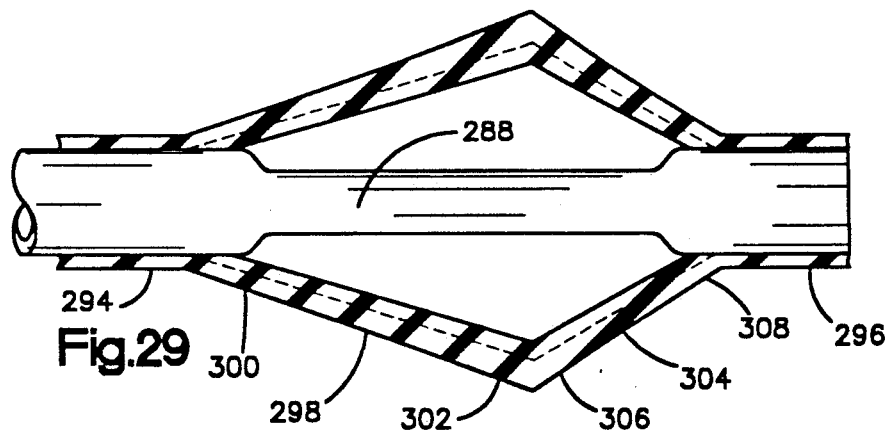
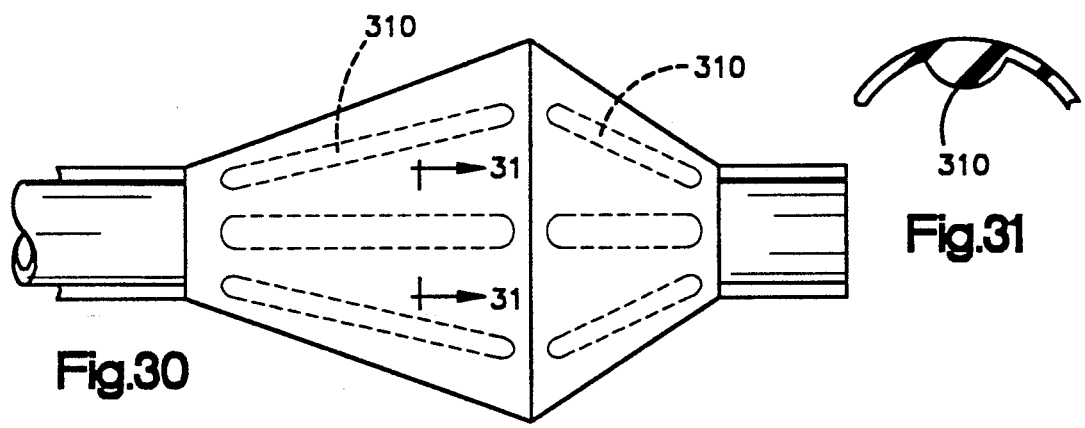

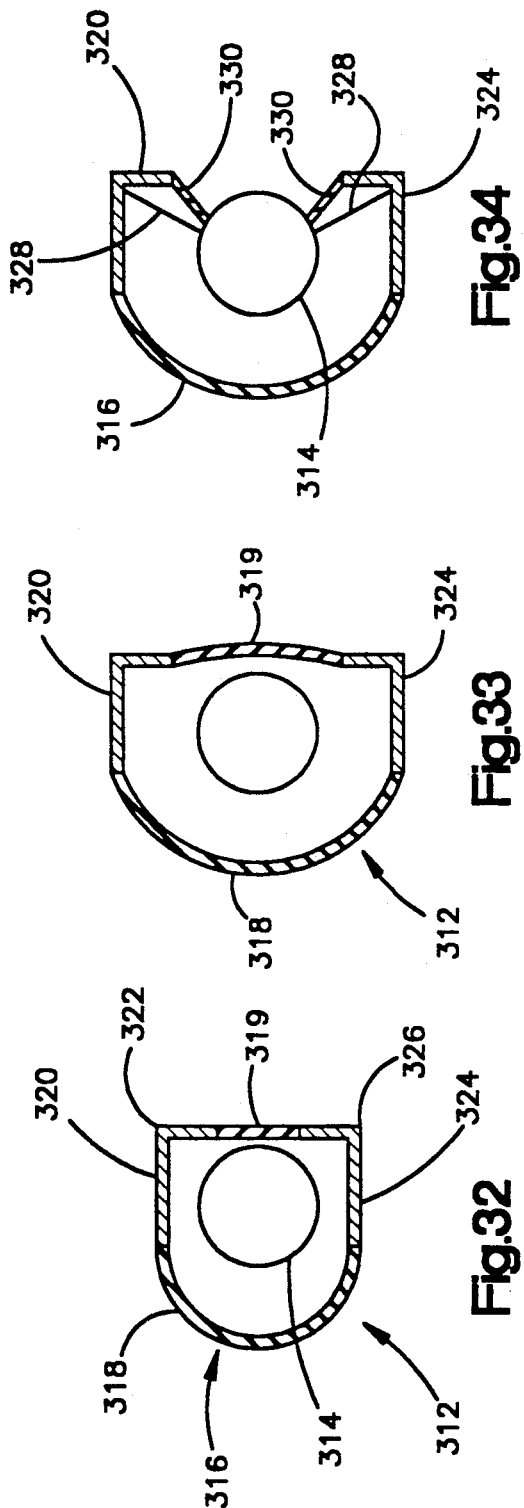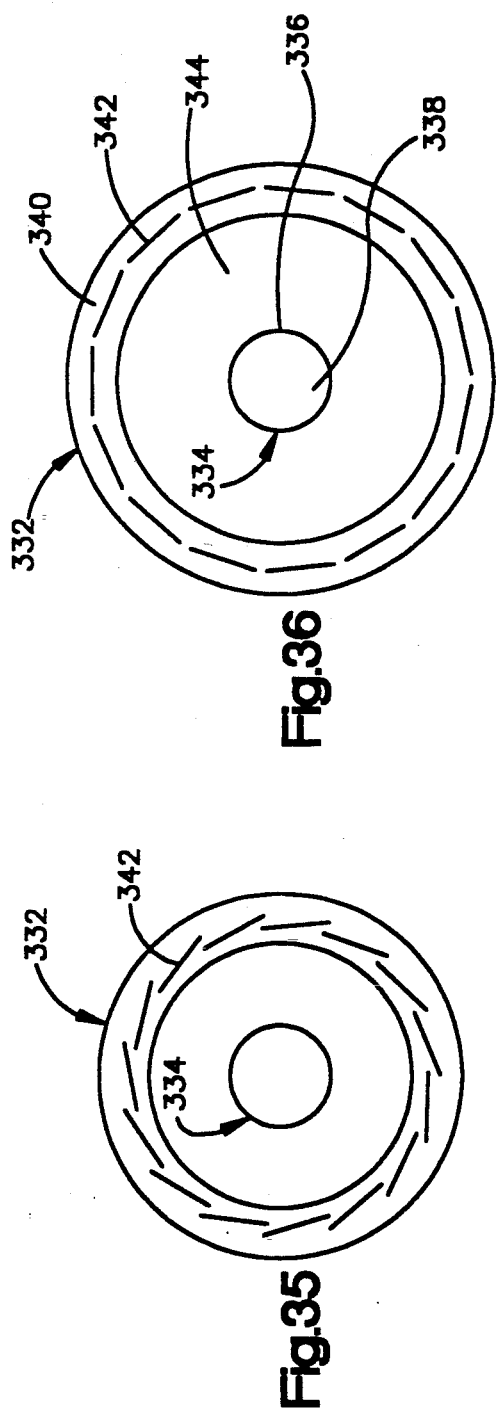

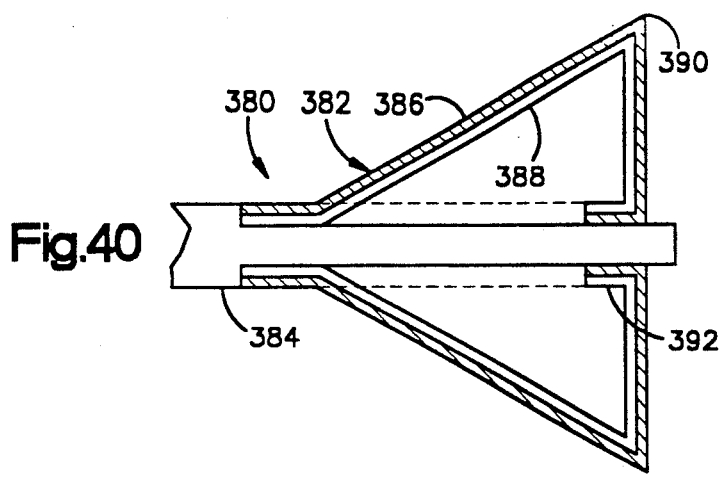
Fig.40
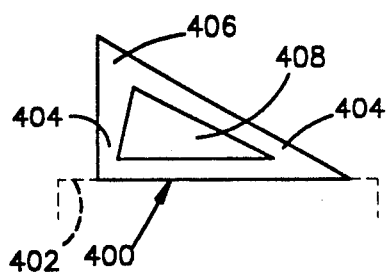
Fig.41A
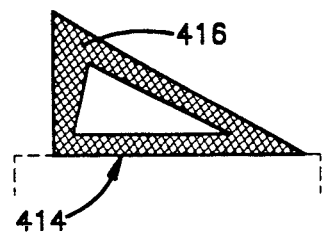
Fig.41B
Fig.41C
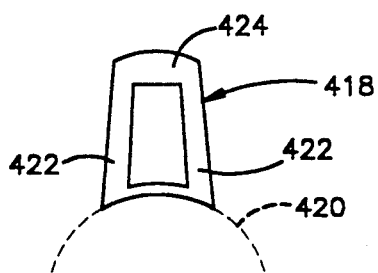
Fig.42A
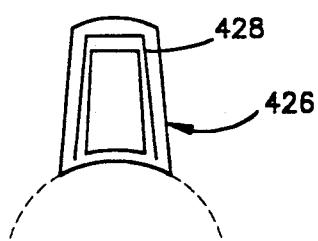
Fig.42B
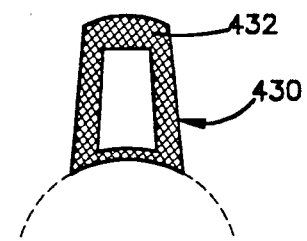
Fig.42C
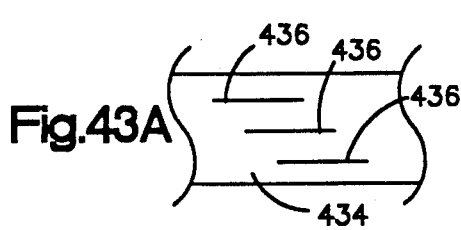
Fig.43A
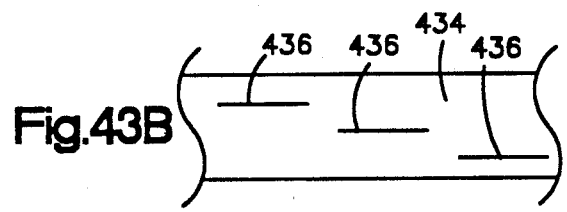
Fig.43B
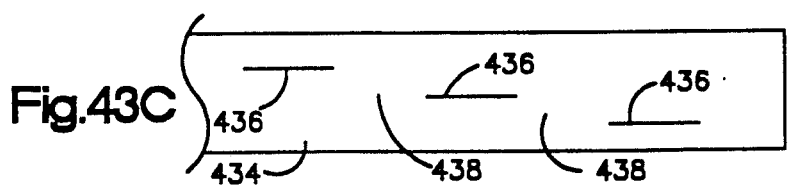
Fig.43C

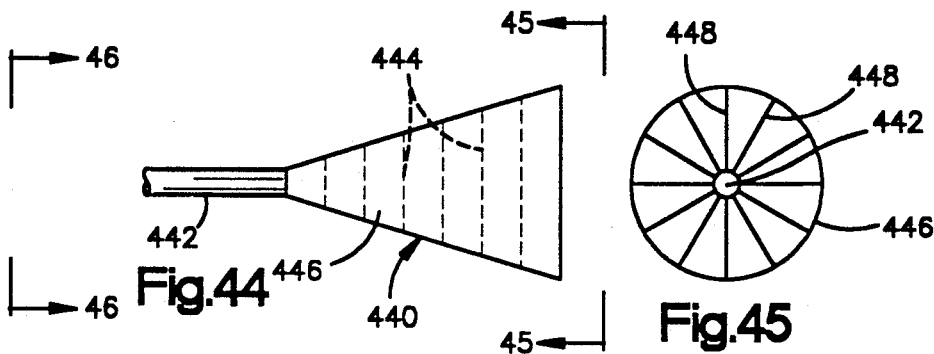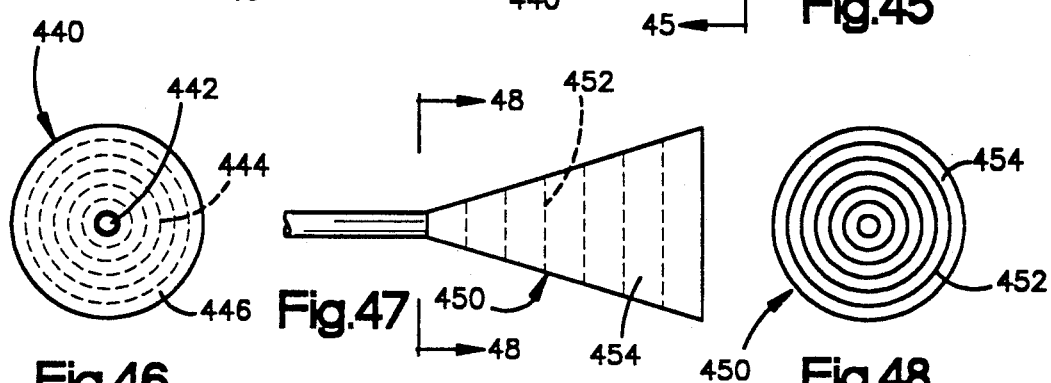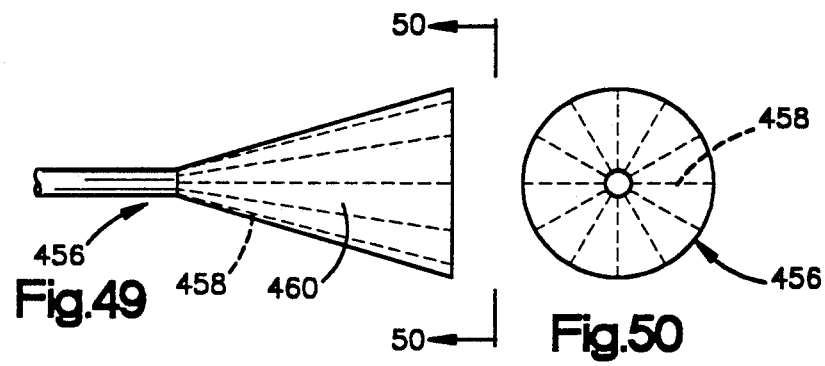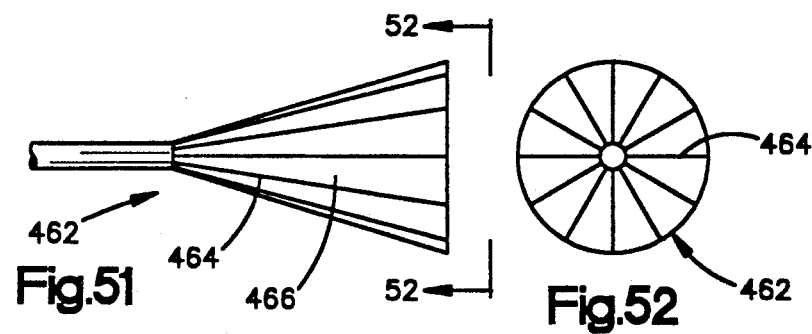

ACTIVE CANNULAS

BACKGROUND OF THE INVENTION

The present invention relates to medical devices, and particularly to expandable medical devices such as cannulas, catheters, retractors, and similar devices.

Existing cannulas as used in endoscopic surgery today are passive devices which are fixed in length and width. They can not be varied intraoperatively in length and width to accommodate larger devices or varying size devices through the skin.

Skin and subcutaneous (subsurface) tissues are viscoelastic: they will gradually stretch without tearing. Once the tissue is slowly stretched it maintains its expanded condition for a period of time. Alternatively, the tissue can be stretched further, for example to progressively stretch out an incision. Then, after relaxation, the tissue will regain its original unstretched condition without having been damaged.

GENERAL DESCRIPTION OF THE INVENTION

The present invention is described herein as relating to cannulas. A cannula is a device for insertion into or through body tissue to provide a working passage for surgical instruments, scopes, etc., as in endoscopic or arthroscopic surgery. A catheter, on the other hand, is an artificial fluid passage primarily used for insertion through an existing body opening. The two types of devices have very different structures and structural requirements. For example, a catheter is usually flexible, very small in diameter, and not suitable for maintaining a working passage through normally closed body tissues, while a cannula is more rigid, larger in size, and designed specifically to provide a working passage for surgical instruments and scopes through normally closed body tissues. It should be understood, however, that many of the features of the present invention can with suitable modifications be applied to the catheter art. Accordingly, the present invention is not limited to cannulas per se, but may be applicable to catheters or other devices also.

The present invention defines an active cannula or sleeve which does more than merely maintain a channel or passage. It is an active device usable to enlarge a channel or passage, to position a scope or instrument, to move or locate tissue, etc. The cannula can vary in size or shape as needed, intraoperatively. Typically, with a passive (non-expandable) cannula, a surgeon must make an incision in the skin and muscle large enough to receive the largest instrument to be passed through the incision to the surgical area. Because a cannula of the present invention is expandable, the surgeon can make a small relatively small incision, stretch the tissue with the expandable cannula, contract the cannula and remove it, allowing the skin to come back to its unstretched condition. Thus, a smaller incision can be made to fit the same size instrument. This results in less trauma and scarring and an easier operation.

Further, known cannulas are generally round, while skin expands (from an incision) in an elliptical fashion, between tissue planes. Thus, the present invention provides cannulas which are or can assume such a noncircular shape, to fit into the natural opening and cause less trauma.

The devices of the present invention are usable in endoscopic procedures generally. The devices can be used to seal off a space; to expand an existing space or a potential space for working or visualization; to move tissue (for example, to stretch an incision) or to protect it. Other uses within the skill of the art but not enumerated herein are within the scope of the invention.

CANNULAS

The cannulas of the present invention allow for the progressive stretching of an incision in skin or subsurface tissue in order to allow improved exposure, while minimizing damage to the tissue by making the actual incision as small as possible.

In the arthroscopic model, a fixed cannula is placed through the skin to the subsurface tissues into a joint. Different size working devices (shavers, burrs, scissors, punches, scope, etc.) are placed through the cannula to visualize or to work in the subsurface area at the distal end of the cannula. The cannula can be progressively expanded or stretched radially outwardly, to stretch or expand the skin and subsurface tissues. The cannula typically expands along its entire length, although it may in some cases be expandable at selected portions along its length.

The expansion can be in a circular pattern, or it can be in an oval or elliptical or other pattern to accommodate (a) the tissue planes or (b) the instruments being inserted through the cannula.

The cannula can expand inwardly to act like a valve or a seal. Or it can expand both inward and outward.

The cannula is preferably flexible—that is, it is bendable about an axis extending perpendicular to the longitudinal extent of the cannula. In other words, the cannula as a long straight object is not rigid but can bend so that it is not straight. This allows the cannula to conform to the body tissues to the extent desired.

All cannula bodies can be multi-lumen for passages through which extend structure for control of bladders, tools, scope, etc.

In a first embodiment, a cannula may be of a stretchable material (such as a polymer) which is introduced into the body with a trocar. The trocar is then removed. Progressively larger dilating devices are placed inside the stretchable cannula, as needed, to progressively stretch out the skin and tissue to a larger size in order to introduce larger instruments through the cannula. Each time the cannula is enlarged, the stretched tissue remains in its stretched condition for a period of time because of its viscoelastic properties.

One way of stretching the cannula is by placing inside the stretchable cannula a bladder (round or elongated in the shape of a sausage, for example) which can be inflated to uniformly stretch the cannula and tissue. The bladder can be deflated and removed, leaving the enlarged opening.

In a second embodiment, the cannula is itself inflatable for expansion. The cannula is basically an inflatable cylinder with expansions in both the inner diameter and the outer diameter. As inflated, the device expands to a preformed shape with the inner diameter following the outer diameter and expanding outward to create a progressively larger opening. Filaments or cords can be placed between the inner and outer walls to limit their separation from each other. The inner wall can be more rigid.

In a third embodiment, the cannula includes one or more stretchable (inflatable or expandable) parts and one or more non-stretchable parts. The non-stretchable parts can be metal or plastic pieces such as curved plates, joined by the stretchable elements which extend longitudinally between them. These stretchable elements can be bladders. As larger devices are passed through the cannula, the stretchable portions expand and the plates move outwardly to stretch an appropriate opening.

In any of these cases, one can monitor and control the amount of pressure being applied to the tissue upon expansion of the cannula, so as to not exceed a certain critical pressure and damage tissue. This can be done by monitoring the actual size of expansion, the amount of air or fluid introduced to inflate the device, the fluid pressure within the device, etc.

CANNULA-BLADDER COMBINATIONS

There are numerous possibilities of a cannula-with-bladder or (catheter-with-bladder) construct.

One specific example is an arthritis irrigation system. This is a multi-lumen tube which has one lumen/portal for inflow of irrigation fluid and a second portal for suction (return). The tube is flexible and has its distal end placed in a joint to be irrigated. The tube is fixed in place by an expanding device as discussed below. Fluid flowing through the joint flushes out debris in the joint. The device can include third or additional lumens for a scope or tools to pass through. Since the tube is both flexible and fixed in place, it can remain in the patient even when the patient is ambulatory. It thus provides a permanent passage for the surgeon to access the joint.

There can be multiple bladders at a location on the cannula, independently controlled, to position the cannula. At least one bladder is preferably at the tip of the device to expand or stretch tissue or to stabilize the device.

In any of the illustrated embodiments, the bladder can be made of a different material from the cannula, as opposed to, for example, a Fogarty catheter which is made of all one material. This will allow for variations in construction, with the bladder being made of one material to better perform its functions and the cannula or other supporting member being made of another material to better perform its functions.

BLADDERS

The expanding (inflatable) bladders of the present invention are constructed in various manners as set forth below. The bladder can stretch cannula walls. The bladder can move tissue and allow selective manipulation of tissue, even arthroscopically. The bladder also has a tamponade effect, lessening bleeding in the surrounding tissues.

The bladder also distributes the retractive force, reducing stress on delicate tissues such as nerve tissue.

There can be one or more bladders at any given location or on any given instrument. Multiple bladders can be controlled as independent structures or as one unit. Specific structure and control is based on the particular application.

The surface of the material can be pebbled or roughened or ridged, or have serrated edges, to better grip tissue and hold the retractor in position. Of course, the surface must still remain smooth enough so that the retractor is easily removable without damage to the tissue it contacts.

The bladders can expand by well in excess of 200%.

MATERIALS

The bladder is preferably made of an elastomeric material which is strong enough to move tissue as desired. A suitable material for the expandable bladder is Silastic ® elastomer, which is available from Dow Corning in medical grades. Other suitable materials are silicone, or latex, or PVC.

The bladder may be made of a non-elastomeric material which is strong enough to move tissue as desired. A suitable material is Mylar ® fabric. A non-elastomeric material may have a more controllable shape because it will not stretch. A non-elastomeric material will collapse inward automatically due to the pressure of the tissue around it, whenever it is not inflated. Many of the illustrated embodiments which are discussed as being made of an elastomeric material can also be made of a non-elastomeric material.

The expandable bladder can be made of a biodegradable material. In such a case, the biodegradable portion can be made detachable from the remainder of the retractor, so that it can be detached and left in the body after surgery. This is useful, for example, to prevent adjacent tissue planes from scarring together after surgery. The biodegradable mass will in time disappear, allowing the tissues to adjoin after they are healed.

The bladder can be made of a composite material—that is, a particle or fiber-reinforced material. Many suitable materials are in use in industry. Composite materials can be made stronger while still retaining flexibility and fluid-sealing capabilities. Composite materials also provide the capability to have a bladder assume a specific shape upon expansion.

The bladder can be made of a composite biodegradable material.

The bladder(s) can be made of two different materials bonded together, such as a stretchable (low-modulus) and a non-stretchable (high-modulus) material. Mylar ® and Silastic ® are suitable materials, or metal for a stiff material. As the inflation fluid (typically air) is introduced, it takes the path of least resistance and the non-stretchable material fills out to its expanded shape first. Then the stretchable material expands, in a manner constrained by the already-expanded non-stretchable material.

The bladder can be made of a transparent material to provide a better view of the operating area and improved visualization.

The bladder may have a dual durometer layered construction, with a thin layer for fluid retention overlying a thicker layer for shaping. Other laminated constructions are possible, also.

SHAPE CONTROL

The external shape of the retractor when expanded, and the amount of expansion, are designed for the specific application on which that retractor is to be used. For example, if the surgeon is working against bone, he can select a retractor which is configured so that it stays flat against the bone, and expands away in the opposite direction, to push tissue away from the bone and create a working and visualization space next to the surface of the bone.

There are several ways to control shape of expansion-thick and thin areas (gaps, ridges, stiffened areas, etc.), fiber reinforcing, dual durometer construction, different materials affixed together, tethering cords, and preshaping.

Upon application of a given amount of force, a thinner material will stretch more than a thicker material. Thus, all other factors being equal, an inflatable device will stretch more where it is thinner, and will stretch less where it is thicker. This occurrence can be used to control the shape into which a bladder expands when it is inflated by fluid under pressure.

As a simple example, it can readily be seen that if a bladder has one half made of a very thick material and one half made of the same material but much thinner, then upon the introduction of fluid under pressure, the thin material will stretch more quickly (easily), and the bladder will expand unevenly. The thin half of the bladder will deform more under the same pressure until the force needed to stretch it further is equal to the force needed to stretch the thicker material. The half made of the thicker material will then begin to stretch, also. (Thus, the thickest point on the wall will be at the crown area (farthest out).)

The areas of variation in cross section can be of various shapes and directions to control the expansion rates. For example, the circumference of a bladder can be configured as an incomplete hoop. Thus, most of the circumference is of a thicker material, while selected areas are thinner. Upon the introduction of fluid under pressure, the thinner areas will expand first, with each thicker area moving outwardly as a whole.

There can be ribs around the circumference. Areas of thickness or thinness can extend longitudinally, circumferentially, radially, or in broken segments.

A second way to control the shape of expansion is the use of a fiber reinforced (composite) material. The direction of the fibers, along with their number, spacing, layering, and length, controls the rate of expansion of the matrix material. Also, areas devoid of fibers will expand faster or further than areas with more or stiffer fibers.

Specifically, the fibers resist stretching along their length. Thus, the bladder will stretch more in a direction across the fibers, or where the fibers are not present, than in a direction along the fibers. Fibers can be placed at the edge of the bladder to maintain the shape of the bladder when inflated. Fibers can be layered, with one layer in one direction and another layer in another direction to control expansion in the other direction. Fibers can be placed in overlapping layers, to allow expansion in one plane only.

Adding fibers makes the bladder more puncture and tear resistant. Note that the bladder can, for this purpose, also be made of or include a self-sealing material.

A third way of controlling expansion shape is to pre-shape the bladder to assume a certain form when expanded. This is done in the molding process. The bladder is typically formed on a mandrel which is of a particular shape and which is sized about half way between the unexpanded and the expanded size of the bladder.

The pre-determined shape of the unexpanded bladder is basically a combination of varying wall thickness and ribbing, made on a three part mold.

In certain experimental models constructed to date, the bladder is bonded onto a nylon stalk of 7 mm O.D. The bladder is stretched from about 3 mm to about 7 mm at its smallest dimension. This pre-stretched area puts the material under tension. Any larger diameter portions are relaxed. As the bladder is expanded, the smaller diameter portion, which is already partially expanded, stretches at a limited rate. The larger diameter portion (under no load) expands at a faster rate. They balance out at a point where all the material is under basically the same load in tension. This is the point at which the shape is attained.

It should be understood that this particular example and its dimensions are not limiting, and that any diameter can be used. This is an example of a specific sized cannula for a specific application.

With a typical material (silicone), the more you stretch the material, the more force is needed to stretch it further.

The prestretching of the bladder is done so that the bladder lies flat on the cannula body. The bonding areas are such that as the expansion takes place the material expands radially outwardly as well as axially.

It can alternatively be doubled up at a certain area, such as the tip of a stalk or cannula. This will allow maximum expansion at the tip.

Tethering cords can be fixed to bladder portions and extend between them to control and/or limit the expansion of the bladder. This can be done with bladders made of a composite material or including plates or other thicker areas. In a cannula construct, the tethering cords can run between the cannula body to the crown of the bladder to control and/or limit its expansion.

Plates can be added in which will limit the shape of the bladder or create an edge. For example, if a flat plate is added, the bladder can expand in a circular fashion but the flat plate will remain flat and provide a flat area on the outside of the bladder. Or the plate can be circular, or at an angle to create an edge. There can be multiple such plates added to create specific shapes. Tethering cords can be used to extend to the plate. This can be useful in the cannula construct.

The bladder can also have a bellows-type construction for increased expansion control and structural rigidity.

Suction can be used to collapse any of the devices to facilitate removal.

BRIEF DESCRIPTION OF THE DRAWINGS

The foregoing and other features of the present invention will become apparent to one skilled in the art upon a consideration of the following description of the invention with reference to the accompanying drawings, wherein:

FIG. 5 is a transverse sectional view through an expanding cannula;

FIG. 6 is a view of the cannula of FIG. 5 in an expanded condition;

FIG. 7 illustrates a cannula having an outwardly expanding bladder formed within the wall of the cannula;

FIG. 8 illustrates a cannula having an inwardly expandable bladder formed in the wall of the cannula;

FIG. 9 illustrates a cannula having an inwardly and outwardly expanding bladder formed within the wall of the cannula;

FIG. 10 illustrates the expansion of a cannula having viscoelastic walls by means of an inserted inflatable member;

FIGS. 11-13 illustrate a cannula comprising a cylinder expandable along its entire length;

FIG. 14 illustrates an elliptical or an oval-shaped cannula having tethering cords;

FIG. 15 illustrates a square-shaped cannula having tethering cords;

FIG. 16 illustrates a cannula having a tethering cord connecting a balloon portion to the cannula wall;

FIGS. 20-25 illustrate longitudinally extending radially expansible cannula segments;

FIGS. 28-31 illustrate a cannula having an expandable bladder portion with a varying wall thickness;

FIGS. 32-34 illustrate flexible bladder portions having relatively rigid members molded therein;

FIGS. 35 and 36 illustrate rigid members molded into the elastomeric material of an inflatable bladder circumscribing a cannula or other medical device;

FIG. 40 illustrates an expanding device having an expanding bladder made of a plurality of materials laminated together;

FIGS. 41A-41C illustrate triangular-shaped expanding portions;

FIGS. 42A-42C illustrate trapezoidal-shaped expanding portions;

FIGS. 43A-43C illustrate the use of overlapping and/or incomplete fibers for expansion control;

FIGS. 44-52 illustrate a variety of bladder devices including reinforcing fibers and/or tethering cords.

DESCRIPTION OF PREFERRED EMBODIMENTS

Figure 1:
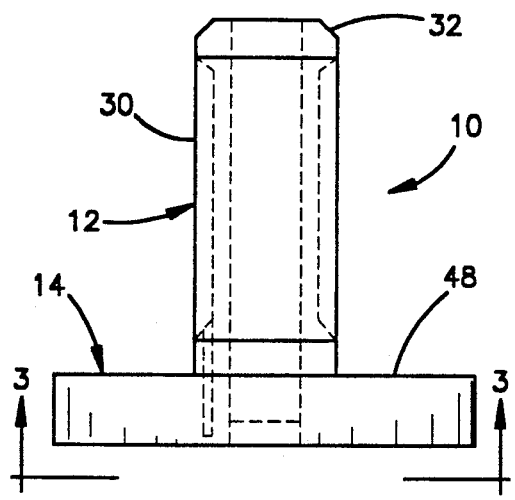
FIG. 1 is a side elevational view of a joint irrigation apparatus embodying the present invention.
Figure 2:
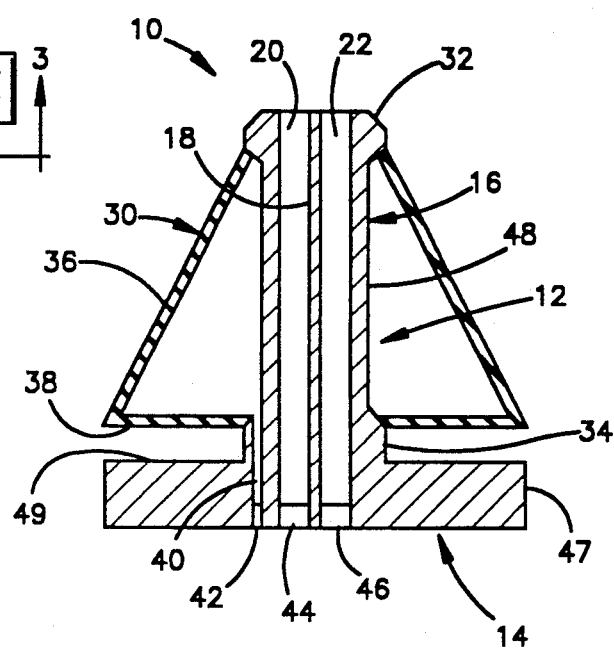
FIG. 2 is a longitudinal sectional view through the apparatus of FIG. 1.
Figure 3:
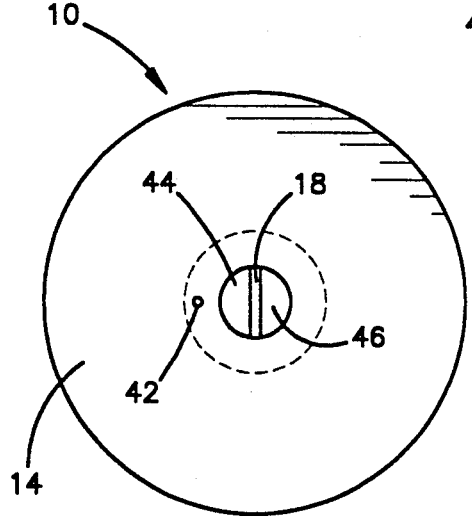
FIG. 3 is a view taken along line 3—3 of FIG. 1.

FIGS. 1-3 illustrate an arthritis irrigation apparatus 10 in accordance with the present invention. The irrigation system 10 includes a cannula 12 having a disc portion 14 and a longitudinally extending cannula body 16. A central wall 18 divides the cannula body 16 into two longitudinally extending lumens 20 and 22.

An expandable bladder 30 is connected to or formed integrally with the cannula 12 at the distal end 32 and proximal end 34 of the cannula body 16. The expandable bladder 30 includes a longitudinally extending wall portion 36 and a transversely extending wall portion 38. The expandable bladder 30 is supplied with fluid under pressure through a fluid supply port 40 closed by a rubber diaphragm seal 42. The lumens 20 and 22 are closed by similar diaphragm seals 44 and 46, respectively. The cannula body 16 has a recessed portion 48 in which the bladder 36 fits when unexpanded.

The system 10 is inserted into a pre-made opening until the disc portion 14 engages the skin. Upon the introduction of fluid under pressure into the expandable bladder 30, the bladder 30 expands from the unexpanded condition illustrated in FIG. 1 to the expanded condition illustrated in FIG. 2. The bladder wall 36 moves radially outwardly, and skin or other tissue is trapped between the bladder wall 38 and the distal surface 49 of the disc portion 14 of the cannula 12.

The system 10 is thus locked in place, with the distal end 32 in position in a joint. Appropriate instruments may then be inserted through the diaphragm seals 44 and 46 into the lumens 20 and 22, respectively. For example, flushing fluid may be supplied to the joint through the lumen 20, while it is removed from the joint by suction through the lumen 22. When the joint is not being flushed, the diaphragm seals 42, 44 and 46 seal the openings in the system 10, and the expanded bladder 30 retains the system 10 in place in the body.

It should be understood that any number of lumens, other than two, can be included in the cannula body 16. The number of lumens is limited only by the size of the instruments to be inserted through the cannula body 16. In a preferred embodiment, the disc portion 14 of the cannula body 12 is about the size of a nickel, with the cannula body 16 being correspondingly smaller. Of course, the dimensions and arrangement of the various portions of the system 10 could be modified to enable the placement of other instruments through the cannula body 16.

Each of the lumens may have a controllable inflow-outflow portal. These can be substituted for the diaphragm seals. These portals may be a simple tube with an on-off valve attached, as is known in the art, or can be another suitable structure.

Figure 4:
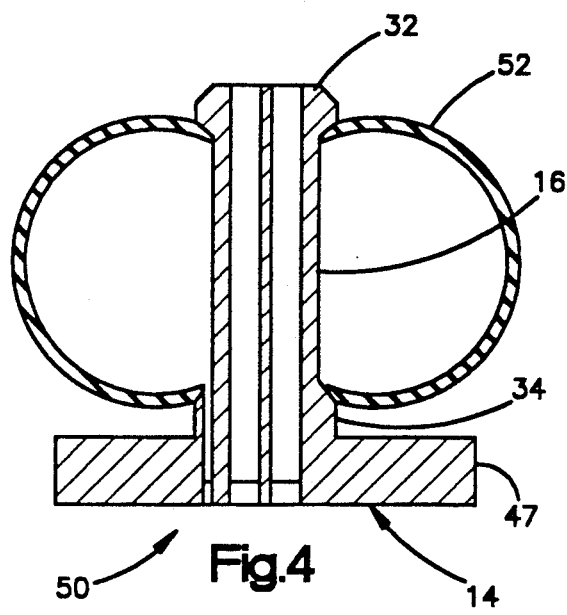
FIG. 4 is a view of an alternate embodiment of the apparatus of FIG. 1.

FIG. 4 illustrates an alternate embodiment of the system 10 in which a system 50 includes a round or doughnut-shaped bladder 52 extending between the distal end 32 and the proximal end 34 of the cannula wall 16. This doughnut-shaped bladder can be easier or less expensive to manufacture, and also can provide more cushioning effect to the tissues which it engages. Again, tissue is trapped between the bladder 52 and the disc portion 14 of the cannula 12, to retain the system 50 in place in the body.

FIGS. 5 and 6 illustrate a variable size cannula in which inflatable bladders push apart two relatively rigid portions to move tissue. FIGS. 5 and 6 are transverse cross sections through a longitudinally extending cannula 60, which can be any desired length. The cannula 60 expands radially outwardly along its length.

The cannula 60 includes a first C-shaped portion 62 having ends 64 and 66 and a second C-shaped portion 68 having ends 70 and 72. An inflatable bladder 74 has one end portion 76 fixed to the end portion 64 of the portion 62. The opposite end portion 78 of the bladder 74 is fixed to the end portion 70 of the portion 68. Similarly, a bladder 80 has one end portion 82 fixed to the end portion 66 of the portion 62, and its second end portion 84 fixed to the end portion 72 of the portion 68.

The portion 62 has an outwardly facing surface 86 and the portion 68 has an outwardly facing surface 88. The cannula 60 has a central opening 90 which is enlarged in size upon expansion of the bladders 74 and 80 to provide a larger working space while reducing tissue damage. Upon the introduction of fluid under pressure into the bladders 74 and 80, the portions 62 and 68 are moved away from each other to engage tissue with their surfaces 86 and 88, respectively. The relatively rigid portions 62 and 68 provide increased pushing strength of the cannula 60 as compared to a soft inflatable bladder. Further, the cannula 60 also holds its structural shape better and is able to maintain the opening better. Thus, with the cannula 60, a limited incision can be made in the tissue, which incision is then enlarged by the cannula itself rather than with a cutting device. The application of suction to the bladders 74 and 80 causes them to deflate to return the cannula 60 to its unexpanded condition. The tissue is viscoelastic and thus will stretch out during its expansion by the expander 60, and then return to its original unexpanded shape, i.e., the original size of the incision after removal of the cannula. Thus, less tissue damage results.

Cannulas in accordance with the present invention may have one or more bladders as part of the cannula wall. These may create inward or outward expansion. For example, FIGS. 7A and 7B illustrate a longitudinal portion of a cannula 92 having a wall portion 94 defining a central opening 96 through which surgical instruments or the like can be passed. The wall portion 94 includes a portion 98 partially defining a fluid chamber 100 which may be supplied with fluid under pressure through a fluid supply line 102 extending through the cannula wall 94. On the introduction of fluid under pressure into the volume 140, the wall portion 98 of the cannula 92 expands radially outwardly, from the unexpanded condition of FIG. 7B to the expanded condition of FIG. 7A, as a seal or retainer against tissue.

Similarly, the cannula 104 illustrated in FIGS. 8A and 8B includes a wall 106 having an inner portion 108 defining a fluid volume 110. Upon the introduction of fluid under pressure through a supply passage 112 in the wall 106, the wall portion 108 expands radially inwardly to close at least partially the central opening 113 in the cannula 104. The expanding portion 114 of the cannula 104 thus acts as a valve or seal for the central opening 110 of the cannula. This can be very useful if it is desired to close the central opening 110 while leaving the cannula 104 in place in the body tissue. The central passage 113 can also be closed completely. Alternatively, the wall portion 108 can clamp onto an instrument or scope extending through the passage 113 to lock it in place.

In addition to the cannula inner seals or valves formed by the radially inwardly expanding bladder walls, the present invention contemplates cannula inner seals formed by other structures. For example, a simple mechanical seal can be used such as a diaphragm seal like the seals 44 and 46 (FIGS. 1-3). Other forms of mechanical seals can be used, such as a membrane (iris) valve, screw lock, twist lock, or luer lock. It is intended that these alternatives be included within the scope of the invention.

FIGS. 9A and 9B illustrate a cannula 116 having an expanding portion 118 in its wall 120. Upon the introduction of fluid under pressure through a fluid supply passage 122 in the wall 120, a portion 124 of the cannula wall 120 expands radially outwardly while a longitudinally co-extensive portion 126 of the wall 120 expands radially inwardly to partially or completely close a central longitudinally extending passage 128. Thus, the cannula 116 has a portion 118 which expands both inwardly and outwardly. The cannulas of FIGS. 7-9 thus illustrate the principle of expanding either inward or outward or both at selected axial locations along the longitudinal extent of a cannula.

FIGS. 10A-10C illustrate the expansion of a stretchable cannula by an expandable member inserted therein. A cannula 130 has a wall 132 defining a central longitudinally extending passage 134. The cannula 130 is made of a stretchable material having viscoelastic properties whereby the wall 130 when stretched outwardly will retain its stretched condition for a period of time. An expander 136 includes a stalk 138 on the end of which is mounted an expanding portion 140. Upon insertion of the expander 136 into the cannula 130 as illustrated in FIG. 10B, the expanding portion 140 may be expanded radially outwardly by the introduction of fluid under pressure through the stalk 138, to stretch a wall portion 142 of the cannula wall 132 radially outwardly. Upon subsequent deflation of the expanding portion 140 of the expander 136, and removal of the expander 136 from the cannula 130, the cannula wall portion 142 remains in its stretched condition for at least a period of time. The cannula 130 is thereby retained in place in the surrounding tissues while instruments or a scope can be passed through it.

The present invention contemplates monitoring the pressure applied to tissue by the expanding cannula. This can be done, for example, with any known pressure sensor or strain gauge. Such is indicated schematically at 144 in FIG. 10C as being on the wall of the device 136 used to stretch the cannula 130. Alternatively, it is indicated schematically at 146 in FIG. 10C as being on the wall of the cannula 130.

FIGS. 11-13 illustrate a cannula 150 which comprises a cylinder expandable along its entire length. The cannula 150 has a central longitudinally extending working passage 152 defined by an inner wall 154. An inflation space 156 separates the inner wall 154 from an outer wall 158 of the cannula 150. A series of tethering cords 160 extend between the inner wall 154 and the outer wall 158.

The inner and outer walls 154 and 158, respectively, of the cannula 150 are constructed so that, upon the introduction of fluid under pressure into the inflation space 156, both walls expand radially outwardly to a larger diameter. fluid is introduced through a fluid inflow means (not shown) which may be a simple tube or valve in fluid communication with the inflation space 156. The cannula 150 expands from the condition shown in FIG. 12 to a further expanded condition as illustrated in FIG. 13. The tethering cords 160 limit movement of the outer wall 158 of the cannula 150 from the inner wall 154 of the cannula 150. In a preferred embodiment, the tethering cords 160 comprise fibers (either solid or stranded) having their ends fixed to the inner wall 154 and the outer wall 158 and extending therebetween. The tethering cords 160 may be unextensible, or they may be somewhat extensible upon the application of a relatively large amount of force. Use of the tethering cords 160 is advantageous in that it allows for controlled expansion of spaced portions of an inflatable device.

The cannula 150 is circular in cross sectional shape. It should be understood that the present invention is not limited to circular cannulas, but specifically contemplates the provision of cannulas of any type described herein of other cross sectional shapes. The cross sectional shape of a particular cannula may be selected in accordance with a particular application for that cannula. For example, an elliptical or oval-shaped cannula 162 (FIG. 14) may be more suitable for insertion between adjacent tissue planes, as it conforms more to the opening between the tissue points. The oval-shaped cannula 162 includes an outer wall 164, an inflation space 166, an inner wall 168, and a working passage 170 extending axially therethrough. Optionally a plurality of tethering cords 172 extend between the inner wall 168 and the outer wall 164, and limit movement of the outer wall 164 from the inner wall 168.

FIG. 15 illustrates, as exemplary of the other shapes of cannulas which may be provided, a rectangular (in this case square) shaped cannula 174 optionally having a plurality of tethering cords 176 extending between the outer cannula wall 178 and an inner cannula wall 180. The inner wall 180 defines a working passage 182 extending longitudinally through the cannula 174.

FIG. 16 illustrates the use of a tethering cord to position a bladder portion relative to a cannula wall. A cannula 190 has an outer wall 192 and an inner wall 194 spaced therefrom. The wall 194 divides the interior of the cannula 190 into a working passage 196 and an inflation fluid passage 198. The passage 198 opens into a bladder 200 fixed at the distal end 202 of the cannula 190. Tethering cords 204 extend between the cannula wall 192 and the crown 206 of the bladder 200. The tethering cords 204 limit movement of the crown portion 206 of the bladder 200 from the cannula wall 192.

The cannula 190 of FIG. 16 is only illustrative of the many ways in which bladder portions can be positioned relative to cannula portions by tethering cords such as the tethering cord 204. The number and positioning and length of the tethering cords determines the relative movement of the various bladder portions to which they are attached, thus aiding in controlling the expanded shape of the bladder relative to the cannula.

Figure 17:
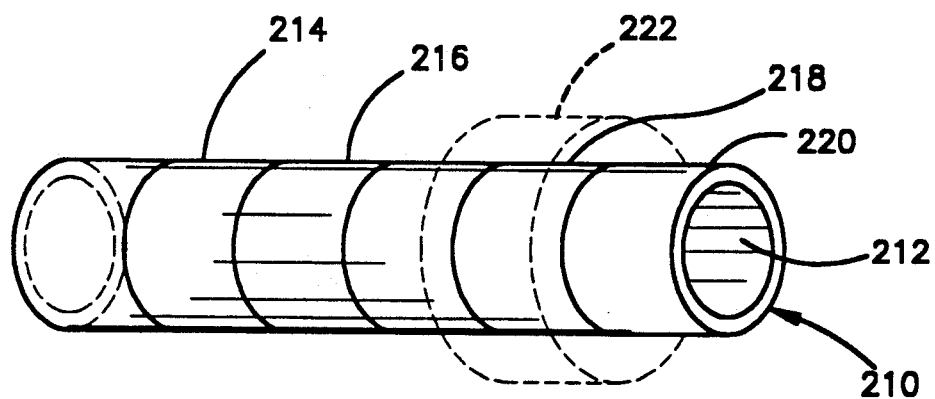
FIG. 17 illustrates a cannula which is selectively expandable at one or more selected longitudinal locations.

FIG. 17 illustrates a cannula 210 which is selectively expandable at one or more selected longitudinal locations. The cannula 210 includes a series of expandable wall segments defining a longitudinally extending central working passage 212. The expandable segments illustrated include a segment 214, a segment 216, a segment 218, and a segment 220. As an example, the segment 218 is expandable, upon the introduction of fluid under pressure, to an expanded condition as illustrated at 222 in FIG. 17. Thus, in accordance with the principles illustrated in FIG. 17, a cannula or other inflatable medical device can be expanded for positioning or sealing at one or more selected longitudinal locations.

Figures 18, 19:
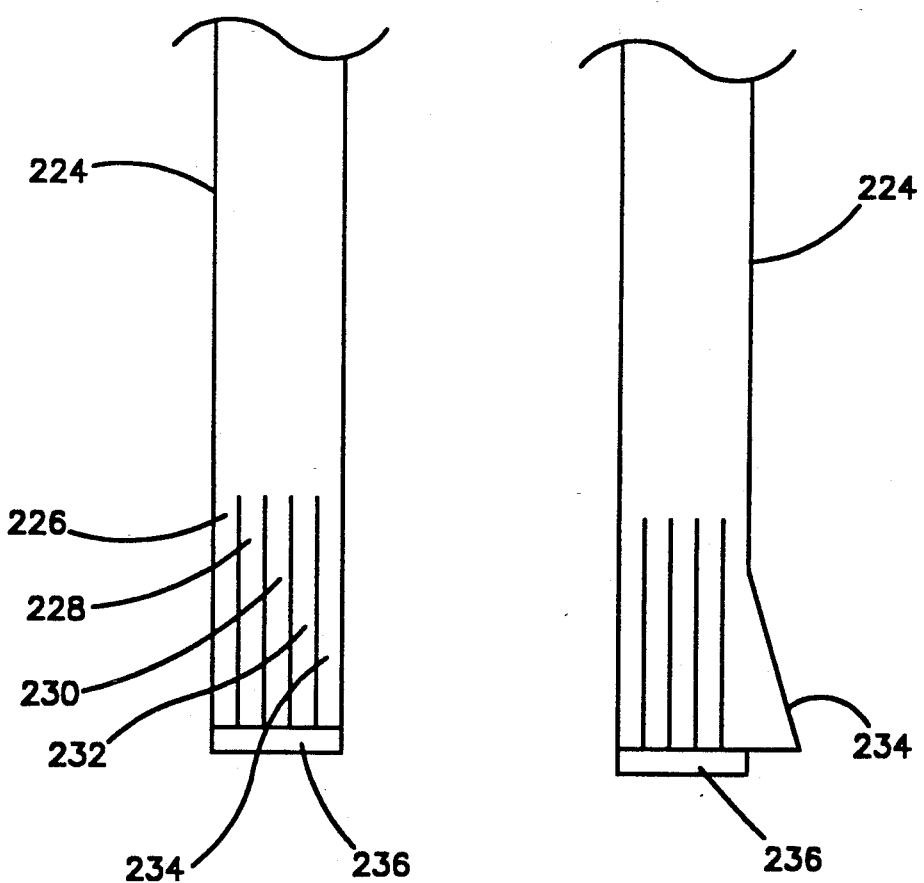
FIGS. 18-19 illustrate a cannula having a plurality of circumferentially spaced expandable segments.

FIG. 18 similarly illustrates a cannula 224 having a plurality of expandable segments 226 through 234 spaced circumferentially around the distal end portion 236 of the cannula 224. Each of the segments 226-234 is selectively expandable, as illustrated in FIG. 19 showing the segment 234 expanded radially outwardly. Accordingly, it is seen that the present invention also contemplates a cannula or bladder, or other inflatable medical device, having a plurality of circumferentially disposed segments expandable radially outwardly upon the selective control of the user of the device. Such selective expansion is useful in selectively positioning the cannula within the tissue in which it is located, in avoiding damage to certain tissue such as nerve tissue, or in protecting or moving certain tissue selectively.

FIGS. 20-25 illustrate such longitudinally extending radially expansible segments of a cannula or bladder or other inflatable medical device in accordance with the present invention. Each segment shown is one of a series of similar segments (not shown) spaced circumferentially around or formed as part of the wall of a cannula or other device 250. The expansible segment 240 illustrated in FIGS. 20-23 is formed as a bellows or accordion and is expandable to a larger extent at its distal end 244 than at its proximal end 242. If the distal end 244 of the expansible segment 240 is located adjacent a distal end of a cannula, the cannula will thus be expandable directly at its tip. The bellows-like construction of the segment 240 provides significant structural rigidity and can transmit in a controlled manner a significant amount of force between its radially outer surface 246 and its radially inner surface 248 adjacent the wall of the cannula 250. The segment 240 is inflated by introduction of fluid under pressure in a known manner into the inflation space 252 (FIG. 23).

The expandable segment 254 illustrated in FIGS. 24 and 25 has a smooth outer skin 256 supported by a plurality of expandable bellows-shaped hoops 258 spaced longitudinally along the length of the segment 254. The skin 256 presents a smooth surface to adjoining tissues upon expansion of the segment 254. The hoops 258 provide structural rigidity to the segment 254, and control the shape of expansion of the skin 256. It should be understood that other configurations of the hoops 258, which support the skin 256 of the segment 254, are contemplated.

Figure 27:
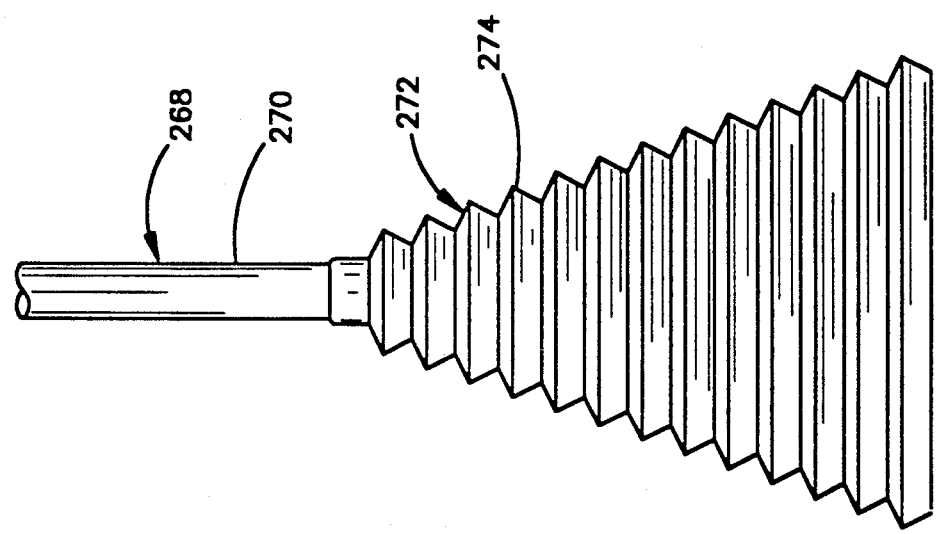
FIGS. 26 and 27 illustrate expandable devices having textured surfaces.
Figure 26:
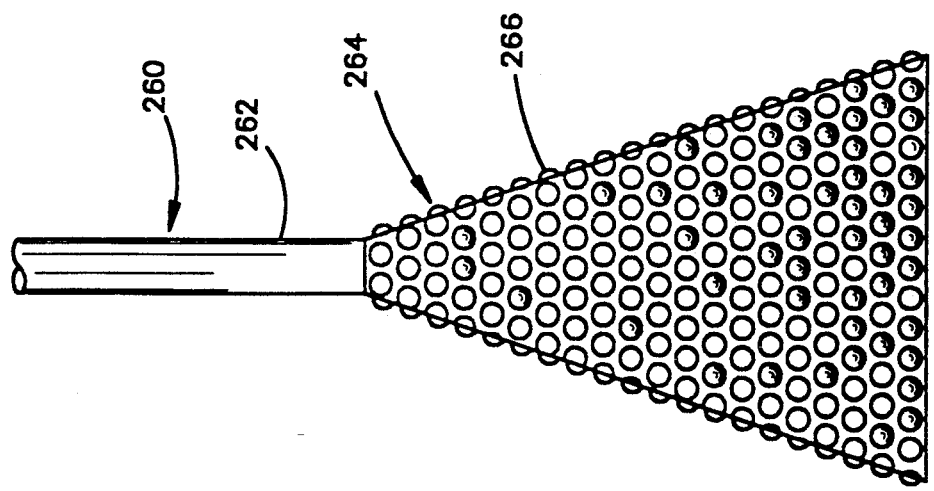

FIGS. 26 and 27 illustrate expandable devices having textured surfaces for grip and location control. The retractor 260 illustrated in FIG. 26 includes a stalk portion 262 and a bladder portion 264 attached thereto. The bladder portion 264 has a pebbled surface 266. The retractor 268 (FIG. 27) has a stalk portion 270 and a bladder portion 272. The bladder 272 has a ribbed surface 274. Other types of texturing or finishing may be provided for an expandable device in accordance with the present invention. Any suitable surface configuration may be used to increase the grip provided between the outer surface of the expandable device and the tissue which it contacts. It should be noted that the surface texturing may also increase the structural rigidity of the expanded device.

FIGS. 28-31 illustrate an expanding device 280 which is preshaped and has a varying wall thickness in its expanding bladder portion. The expanding device 280 includes a support member 282 which may be a solid stalk or a hollow cannula or other member. The support member 282 has a widened proximal portion 286, a narrower diameter central portion 288, and a widened distal portion 290.

Bonded to the support member 282 is an expanding bladder 292. The expanding bladder 292 includes a proximal portion 294 bonded to the proximal portion 286 of the support member 282. The expanding bladder 292 also includes a distal portion 296 bonded to the distal end portion 290 of the support member 282. Extending distally from the portion 294 is a first expanding portion 298 having a thinner wall section at its proximal end 300 and a thicker wall section at its distal end 302. Extending distally from the expanding portion 298 to the thin wall portion 296 is a second expanding portion 304. The second expanding portion 304 is thicker at its proximal end 306 than at its distal end 308, having a tapering cross section between the first expanding portion 298 and the distal end portion 296.

When in the unexpanded condition, the first and second expanding portions 298 and 304, respectively, of the expandable bladder 292 generally lie flat within the recess formed by the narrow portion 288 of the support member 282. Upon the introduction of fluid under pressure into the interior of the bladder 292 through a port (not shown) in the support member 282, the bladder 292 expands from the condition illustrated in FIG. 28 to the condition illustrated in FIG. 29. The expanding portions 298 and 304 expand radially outwardly as illustrated. Because the material of the bladder 292 is thinner at its axially outer end portions 300 and 308, that material stretches more and so the thicker portions 302 and 306 move radially outwardly the greatest amount. The proximal and distal end portions 294 and 296, respectively, are prestretched, that is, stretched to a diameter greater than their relaxed condition, for insertion over the support member 282.

Thus, it is seen that the wall thickness of a bladder can be varied at selected locations to control the rates and distances of expansion of the bladder portions. Further, portions of the bladder can be prestretched so that they reach their maximum elongation at an earlier amount of expansion. These factors can be used to control the expanded shape of the bladder.

In addition, there may be provided ribs such as the longitudinally extending ribs 310 illustrated in FIGS. 30 and 31 which are of an increased wall thickness to provide structural support and expansion control of the elastomeric material of the bladder. The ribs 310 are illustrative of any region of increased wall thickness used to control the shape of expansion. Such regions may run longitudinally as illustrated in the device 280, or may run transversely or circumferentially or in other directions. Taken in combination, all of these factors are usable to control the shape of expansion of an inflatable medical device.

In accordance with a further embodiment of the invention, relatively rigid members such as plates may be molded into relatively flexible bladder portions to define edges and surfaces, as illustrated in FIGS. 32-34. A medical device 312 (FIG. 32) includes a support member 314 such as a cannula to which is attached an expanding (elastomeric) bladder 316. The attachment between the bladder 316 and the support member 314 is not shown in these particular cross-sectional views, but may be in any manner known or as described herein. The bladder 316 has an elastomeric curved portion 318 and an elastomeric portion 319. A plate 320 is molded into the bladder 316 and has an edge 322. A second plate 324 molded into the bladder 316 has an edge 326. Upon the introduction of fluid under pressure into the volume between the support member 314 and the bladder 316, the bladder expands radially outwardly from the condition shown in FIG. 32 to the condition shown in FIG. 33. Although the elastomeric portion 318 of the bladder 316 changes dimensions, the plates 320 and 324 do not. Thus, the expanding device 316 includes flat surfaces and edge surfaces which move radially outwardly and maintain their rigid condition upon expansion of the device 312. The plates 320 and 324 thus control and partially define the expanded shape of the device 312.

Alternatively or additionally, as illustrated in FIG. 34, tethering cords 328 may be employed between the support member 314 and the plates 320 and 324. The tethering cords 328 also serve to control and/or limit expansion of the device 312. Additionally, it can be seen that the device of FIG. 34 includes elastomeric bladder portions 330 extending directly between the plates 320 and 324 and the support member 314. Again, this is an alternative form of the construction. Expanding bladders constructed in accordance with the present invention can use any one or more of these various means of controlling or limiting the expansion of the inflatable medical device, in order to achieve the optimum structure for the particular application.

FIGS. 35 and 36 further illustrate the use of rigid plates or members molded into elastomeric material of an inflatable medical device. An expanding bladder 332 is fixed circumferentially by means not shown around a cannula 334. The cannula 334 includes a cannula wall 336 defining a longitudinally extending central opening 338. The expanding bladder 332 includes an elastomeric material 340 within which are molded a series of relatively rigid plates 342. Between the expanding bladder 332 and the cannula wall 336 is a fluid inflation space 344. Upon the introduction of fluid under pressure into the inflation volume 344, the expanding bladder 332 expands radially outwardly from the condition shown in FIG. 35 to the condition shown in FIG. 36. The elastomeric material 340 stretches and elongates circumferentially. The areas of the elastomeric material 340 which are devoid of plates 342 stretch further, thus allowing the plates 342 to separate. The plates 342, which were previously in overlapping position, are separated as illustrated in FIG. 36. The plates 342 impart structural rigidity and strength to the elastomeric material 340. The invention is not limited to the particular configuration of rigid plates and elastomeric material illustrated, but contemplates any such configuration of relatively rigid members or portions in a relatively stretchable matrix material.

Figure 37:
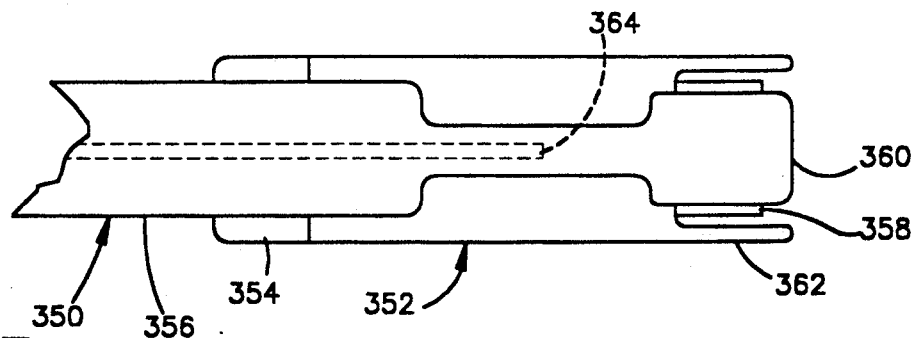
FIGS. 37 and 38 illustrate a cannula having a bladder with a doubled-over bladder portion.
Figure 38:
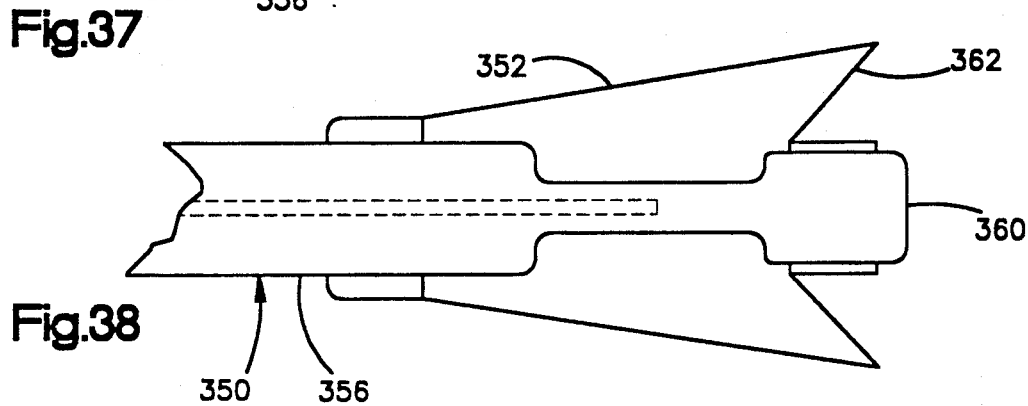

The expanding device illustrated in FIGS. 37 and 38 includes a doubled-over bladder portion to allow maximum expansion at the distal end portion of the device. The device includes a cannula or stalk or other support member 350. An expanding bladder 352 is bonded at 354 to a proximal portion 356 of the support member 350, and at 358 to a distal end portion 360 of the support member 350. The material of the expanding bladder 352 is doubled-over at 362 adjacent the distal end portion 360. Upon the introduction of fluid under pressure into the volume defined by the bladder 352, through a fluid supply port 364, the bladder 352 expands from the condition shown in FIG. 37 to the condition shown in FIG. 38. Because of the doubled-over portion 362 of the bladder 352, maximum expansion is gained at the distal end of the device rather than at the center or at the proximal end of the expanding bladder 352. Again, such a device may include bladder portions having varying wall thicknesses as discussed above, tethering cords, etc., all to control the expanded shape of the device.

Figure 39:
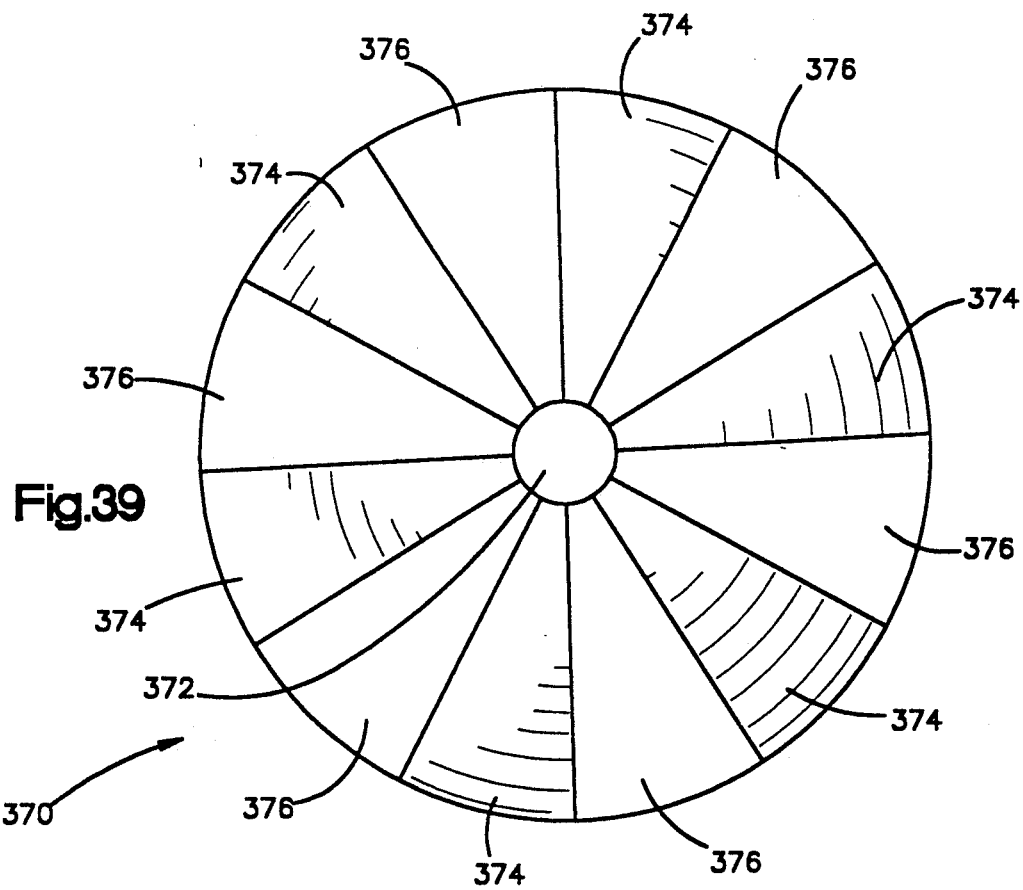
FIG. 39 illustrates an expanded bladder having adjoining portions with different material characteristics.

FIG. 39 illustrates an expanding bladder 370 having adjoining portions with different material characteristics The device is shown in end view as disposed circumferentially around a cannula 372. Alternate portions 374 of the device are made of a first material having a first set of material characteristics, while the interfitted portions 376 are made of a second material having a second set of material characteristics. For example, one material may have a lower modulus of elasticity and the other a higher modulus of elasticity. One may be thicker and the other thinner. One may be elastomeric and the other not. Other combinations are possible. The portions may be bonded together with adhesive, may be heat-sealed together, or may be solvent sealed. One portion can be made of metal. PVC is also a suitable material.

Upon the introduction of fluid under pressure into the expanding device 370, the potions 374 and 376 expand or move at different rates or into different shapes. The adjoining of different materials can be used to control the expanded shape of the device 370.

FIG. 40 illustrates an expanding device 380 having an expanding bladder 382 made of a plurality of materials laminated together. The expanding portion 382 is mounted on a stalk or cannula 384. The bladder 382 includes an outer layer 386 of a first material laminated to an inner layer 388 of a second material. Again, the layers may have differing material characteristics—perhaps polymers with specific properties bonded together. For example, the layer 386 may be of a different durometer from the material of the layer 388. One of the layers may provide structural support while the other provides fluid sealing capabilities. One layer may provide puncture resistance while the other provides expansion shape control. These are some of the many properties available with such laminated structures.

It should also be noted that the expandable bladder 382 has an expanded dimension many times greater than its unexpanded dimension as illustrated in dashed lines in FIG. 40. This is illustrative of the large degree of expansion which the expandable bladders of the present invention are able to generate. For example, expandable bladders in accordance with the present invention have been built having expansion rates of approximately 700% as compared to the unexpanded diameter.

FIG. 41A illustrates a triangular shaped expanding element 400 fixed to a supporting device indicated at 402. The expanding element 400 has relatively thin walled portions 404 and a relatively thick wall portion 406. Upon the introduction of fluid under pressure into the volume 408 defined by the bladder 400, the relatively thin walled portions 404 are stretched to a greater extent than the relatively thick walled portion 406. In the similar expanding segment 410 (FIG. 41B), a fiber 412 is embedded in the elastomeric material of the expanding segment to control and limit its expansion. Again, in the similar expanding segment 414 illustrated in FIG. 41C, a fiber mesh 416 is embedded in the elastomeric material of the expanding segment to strengthen it and to control its expansion.

The expanding segments illustrated in FIGS. 42 and 42C are similar to FIG. 41 in structural composition but are trapezoidal shaped rather than triangular shaped. FIG. 42A illustrates an expanding segment 418 connected with a support member 420. The segment 418 includes relatively thin walled portions 422 and a relatively thick walled portion 424. Upon the introduction of fluid under pressure into the volume defined by the expanding portion 418, the relatively thin walled portions 422 stretch to a greater extent than the relatively thick walled portion 424, whereby the relatively thick walled portion 424 moves radially outwardly to a greater extent. The expanding segment 426 (FIG. 42B) includes an embedded fiber 428 for expansion control purposes. The expanding segment 430 (FIG. 42C) includes an embedded fiber mesh 432 for structural support and expansion control purposes. The structural compositions and uses of embedded fibers and fiber meshes illustrated in FIGS. 41 and 42 are merely illustrative of the various ways in which fibers embedded in the elastomeric material of an expanding medical device can be used to control the expansion thereof.

FIGS. 43A-43C illustrate the use of overlapping and/or incomplete fibers for expansion control. A stretchable material 434 (FIG. 43A) has a plurality of fibers or other reinforcing elements 436 embedded therein. As the stretchable material 434 is elongated, the elastomeric material in the stretch zones 438 (FIG. 43C) between the fiber portions 436 stretches to a greater extent than the material immediately around the fibers 436. Further, the embedded fibers resist transverse expansion of the elastomeric material while encouraging longitudinal expansion as shown. These drawings are merely illustrative of the use of the concept of overlapping fibers with stretch zones to control expansion rates of an elastomeric material used in an expanding medical device such as a cannula or catheter. The present invention contemplates other such arrangements of fibers or reinforcing elements in the elastomeric materials.

For example, FIGS. 44-46 illustrates a bladder retractor 440 fixed to a cannula 442. A plurality of circumferentially extending reinforcing fibers 444 are embedded in an elastomeric matrix material 446. In addition, a plurality of tethering cords 448 extend radially between the cannula 442 and the elastomeric material 446 to limit the radially outwardly expansion. As can be seen in FIG. 46, the reinforcing fibers 444 are not complete but rather are broken fibers extending circumferentially within the matrix material 446 to define stretch zones between them. Alternatively, the reinforcing fibers may be complete, as illustrated in FIGS. 47 and 48. In the retractor 450 illustrated in FIGS. 47 and 48, a plurality of complete circumferentially extending reinforcing fibers 452 are embedded in the matrix material 454. The retractor 456 illustrated in FIGS. 49 and 50 includes a plurality of longitudinally extending incomplete reinforcing fibers 458 embedded in the matrix material 460. The retractor 462 illustrated in FIGS. 51 and 52 includes a plurality of longitudinally extending complete reinforcing fibers 464 embedded in an elastomeric matrix material 466. Again, the invention contemplates other such configurations of reinforcing fibers embedded in matrix materials, and is not limited to those shown.

Figure 53:
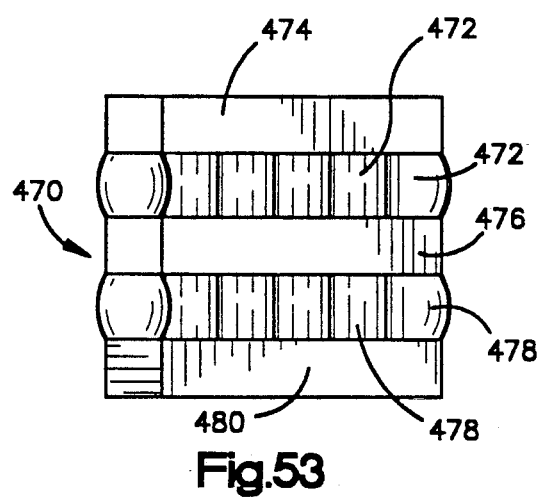
FIGS. 53-55 illustrate a structural unit comprising a series of expandable bladders laminated together.
Figure 54:
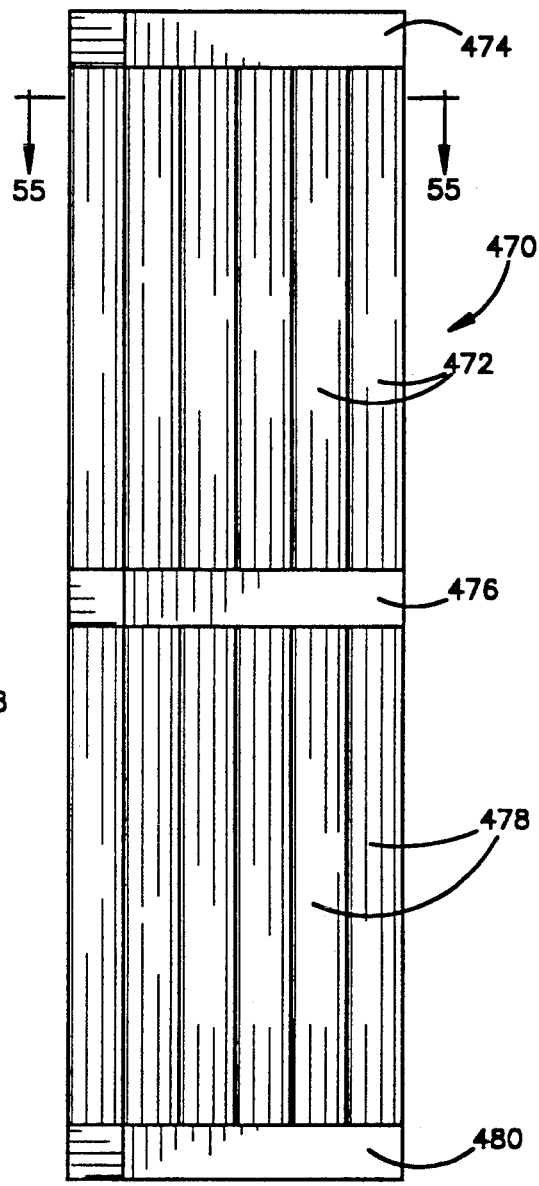
Figure 55:
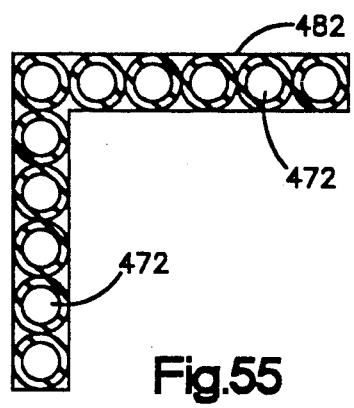

FIGS. 53-55 illustrate a series of expandable bladders laminated together to define a structural unit 470. A series of upper longitudinally extendable bladders 472 have their ends fixed between an upper member 474 and a central member 476. A series of lower longitudinally extending bladders 478 have their ends fixed between the central member 476 and a lower member 480. A covering or retainer 482 (FIG. 55) may enclose all of the units. Upon the introduction of fluid under pressure, the bladders 472 and 478 expand longitudinally from the condition illustrated in FIG. 53 to the condition illustrated in FIG. 54. When the bladders 472 and 478 are fully inflated as illustrated in FIG. 54, they define, together with the members 474, 476 and 480 and the retainer 482, a rigid structural unit. This type of laminated bladder construction will find many suitable uses. It should be understood that other configurations of bladders laminated together are contemplated and are within the scope of the invention.

From the above description of the invention, those skilled in the art will perceive improvements, changes and modifications in the invention. Such improvements, changes and modifications within the skill of the art are intended to be covered by the appended claims.

I claim:

1. An apparatus comprising a cannula for providing a working passage through body tissue, and an expandable bladder extending along and circumferentially around an outer surface of said cannula, said bladder being expandable from a retracted condition to an extended condition, said cannula having a cylindrical proximal portion, a cylindrical distal portion, and a cylindrical intermediate portion disposed between said proximal and distal portions, said intermediate portion having a diameter which is less than the diameter of said proximal portion and which is less than the diameter of said distal portion to form an annular recess which extends around said intermediate portion of said cannula, said bladder having a cylindrical thin-wall proximal end portion which extends around and is secured to said proximal portion of said cannula, said bladder having a cylindrical thin-wall distal end portion which extends around and is secured to said distal portion of said cannula, said bladder having a thick-wall intermediate portion which extends around said intermediate portion of said cannula, at least a portion of said thick-wall intermediate portion of said bladder having a thickness which is at least as great as the combined radial extents of the annular recess which extends around the intermediate portion of said cannula and the distal thin-wall end portion of the bladder, said thick-wall intermediate portion of said bladder being disposed in abutting engagement with an outer side surface of said intermediate portion of said cannula and extending radially outward of the annular recess which extends around the intermediate portion of said cannula when said bladder is in the retracted condition, said thick-wall intermediate portion of said bladder being disposed radially outward of the annular recess which extends around the intermediate portion of said cannula when said bladder is in the extended condition, said bladder having an axially tapering proximal connector portion which extends between said thin-wall proximal end portion of said bladder and said thick-wall intermediate portion of said bladder, said bladder having an axially tapering distal connector portion which extends between said thin-wall distal end portion of said bladder and said thick-wall intermediate portion of said bladder.

2. An apparatus as set forth in claim 1 wherein at least a portion of said axially tapering proximal connector portion is disposed in the annular recess which extends around the intermediate portion of said cannula when said bladder is in the retracted condition and is disposed radially outwardly of the annular recess which extends around the intermediate portion of said cannula when said bladder is in the extended condition, at least a portion of said axially tapering distal connector portion is disposed in the annular recess which extends around the intermediate portion of said cannula when said bladder is in the retracted condition and is disposed radially outwardly of the annular recess which extends around the intermediate portion of said cannula when said bladder is in the extended condition.

3. An apparatus as set forth in claim 1 wherein said cylindrical thin-wall proximal end portion of said bladder is radially stretched by engagement with said proximal portion of said cannula to retard movement of said cylindrical thin-wall proximal end portion of said bladder relative to said cannula, said cylindrical thin-wall distal end portion of said bladder being radially stretched by engagement with said distal portion of said cannula to retard movement of said thin-walled distal end portion of said bladder relative to said cannula.

* * * * *